US006437551B1

(12) United States Patent
Krulevitch et al.

(10) Patent No.: US 6,437,551 B1
(45) Date of Patent: Aug. 20, 2002

(54) MICROFABRICATED AC IMPEDANCE SENSOR

(75) Inventors: Peter Krulevitch, Pleasanton; Harold D. Ackler, Sunnyvale, both of CA (US); Frederick Becker, Houston, TX (US); Bernhard E. Boser, Berkeley, CA (US); Adam B. Eldredge, Austin, TX (US); Christopher K. Fuller, Livermore, CA (US); Peter R. C. Gascoyne, Bellaire, TX (US); Julie K. Hamilton, Tracy, CA (US); Stefan P. Swierkowski, Livermore, CA (US); Xiao-Bo Wang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 2 days.

(21) Appl. No.: 09/704,355

(22) Filed: Nov. 1, 2000

Related U.S. Application Data

(60) Provisional application No. 60/163,109, filed on Nov. 2, 1999.

(51) Int. Cl.[7] ............... G01N 27/00; G01N 33/543; G01R 27/28
(52) U.S. Cl. ............... 324/71.1; 324/649; 436/518
(58) Field of Search ............... 324/71.4, 71.1, 324/609, 601, 649, 525, 693; 428/34.4; 156/99; 436/518

(56) References Cited

U.S. PATENT DOCUMENTS

| 3,836,849 A | 9/1974 | Coulter et al. ........ 324/71 CP |
|---|---|---|
| 3,944,917 A | 3/1976 | Hogg et al. ............ 324/71 CP |
| 4,535,284 A | 8/1985 | Groves et al. ............ 324/71.1 |
| 4,701,826 A | * 10/1987 | Mikkor ....................... 361/283 |
| 4,791,355 A | * 12/1988 | Coulter et al. ............ 324/71.1 |
| 5,572,115 A | * 11/1996 | Strong et al. ............. 324/71.1 |
| 5,575,929 A | 11/1996 | Yu et al. ....................... 216/10 |
| 5,691,633 A | 11/1997 | Liu et al. ................. 324/71.1 |
| 5,888,390 A | 3/1999 | Craig ...................... 210/198.2 |
| 5,890,745 A | 4/1999 | Kovacs ........................ 285/24 |
| 5,932,315 A | * 8/1999 | Lum et al. .................. 428/172 |

FOREIGN PATENT DOCUMENTS

| WO | WO99/14368 | 3/1999 | ............ C12Q/1/68 |

* cited by examiner

*Primary Examiner*—N. Le
*Assistant Examiner*—Anjan K. Deb
(74) *Attorney, Agent, or Firm*—L. E. Carnahan; Alan H. Thompson (57) ABSTRACT

A microfabricated instrument for detecting and identifying cells and other particles based on alternating current (AC) impedance measurements. The microfabricated AC impedance sensor includes two critical elements: 1) a microfluidic chip, preferably of glass substrates, having at least one microchannel therein and with electrodes patterned on both substrates, and 2) electrical circuits that connect to the electrodes on the microfluidic chip and detect signals associated with particles traveling down the microchannels. These circuits enable multiple AC impedance measurements of individual particles at high throughput rates with sufficient resolution to identify different particle and cell types as appropriate for environmental detection and clinical diagnostic applications.

22 Claims, 6 Drawing Sheets

MICROFABRICATED AC IMPEDANCE SENSOR

RELATED APPLICATION

This application relates to U.S. Provisional Application No. 60/163,109 filed Nov. 2, 1999, and claims priority thereof.

The United States Government has rights in this invention pursuant to Contract No. W-7405-ENG48 between the United States Department of Energy and the University of California for the operation of Lawrence Livermore National Laboratory.

BACKGROUND OF THE INVENTION

The present invention relates to microfluidic devices with microelectrodes, more particularly to microfluidic devices, particularly to microfabrication technology for producing microchannels with embedded electrodes, and more particularly to a microfabricated AC impedance sensor for multi-frequency particle impedance characterization.

Microfabrication has become an enabling technology for development of the next generation of analytical instrumentation for performing medical diagnoses, sequencing the human genome, detecting air borne pathogens, and increasing throughput for combinatorial chemistry and drug discovery. These miniature devices take advantage of scaling laws and unique physical phenomena which occur at the micro-scale to perform new types of assays. The large surface area to volume ratio and small size of microfabricated fluidic devices results in laminar flows, increased surface contact between sample fluids and electrodes, fast and uniform heat transfer, and reduced reagent use. Surface tension and viscous forces dominate while inertial effects are negligible. Microfabricated electrodes can produce high electric fields for electroosmotic flows and electrophoretic separations, and large field gradients for inducing dielectrophoretic forces on particles.

The Coulter counter, a commercial instrument which uses DC impedance (resistance) measurements to determine the volume of small particles in suspension, has existed for over 40 years. Instruments that combine Coulter Principle and single high frequency impedance measurements to determine the cellular cytoplasmic conductivity are available for blood cell analysis. However, such two-parameter measurements are incapable of distinguishing between some particle subpopulations of interest (e.g., granulocytes and monocytes, or spores and background particles). What is desired for a host of hematology, pharmacology, forensic, and counter biological warfare applications is a system that can perform broad-band impedance characterizations of particles to enable superior particle differentiation via features in their impedance spectra. Recent research has shown that cellular parameters vary with such physiologic alterations as apoptosis, malarial infection, cell differentiation, and exposure to toxins.

A method often employed for broad-band electrical characterization of particles is electrorotation (ROT), whereby a rotating electric field is used to generate a torque on a particle. The magnitude and direction of the torque, and the resulting particle rotation, depend on the particle's dielectric properties. By measuring a particle's rotation rate as a function of excitation frequency, its conductivity, membrane capacitance, membrane resistance, and other properties can be determined. Although the technique is precise, it requires significant measurement time; even automated ROT systems take several minutes per particle.

A faster approach uses a pulse-FFT measurement scheme. As particles pass through a sensor orifice, a broadband electrical impulse is used to excite them. The particle's impedance signature is then generated using the Fast Fourier Transform (FFT) of the sensor's impulse response. This technique produces a quasi-continuous measure of the particle's impedance spectra, but since the energy of the excitation signal is spread across a band of frequencies, the signal-to-noise ratio (SNR) is inherently worse than in a discrete frequency system.

Another approach involves the use of tuned oscillators to perform simultaneous impedance measurements at multiple, discrete frequencies which are chosen to capture the important transitions in the particle's impedance spectra. Since the system's signal power is concentrated at the measurement frequencies, this technique produces a better signal to noise ratio than the pulse-FFT approach. However, changes in the operating frequencies or solution conductivity may cause the oscillator circuit to become de-tuned. Such a system is most useful for measurements involving predetermined particle types under specific operating conditions.

Microfluidic devices with microelectrodes have the potential to enable studies of phenomena at size scales where behavior may be dominated by different mechanisms than at macroscales. Through work developing microfluidic devices for dielectrophoretic separation and sensing of cells and particles, we have fabricated devices from which general or more specialized research devices may be derived. Fluid channels from 80 $\mu$m wide×20 $\mu$m deep to 1 mm wide×200 $\mu$m deep have been fabricated in glass, with lithographically patterned electrodes from 10 to 80 $\mu$m wide on one or both sides of the channels and over topographies tens of microns in height. The devices are designed to easily interface to electronic and fluidic interconnect packages that permit reuse of devices, rather than one-time use, crude glue-based methods. Such devices may be useful for many applications of interest to the electrochemical and biological community.

The present invention involves a microfabricated flow-through impedance characterization system capable of performing AC, multi-frequency measurements on cells and other particles. The prototype sensor measured both the resistive and reactive impedance of passing particles, at rates of up to at least 100 particles per second. Its operational bandwidth approached 10 MHz with a signal-to-noise ratio of approximately 40 dB. The bandwidth on signal-to-noise ratio may be increased. Particle impedance is measured at three or more frequencies simultaneously, enabling the derivation of multiple particle parameters. This constitutes an improvement to the well-established technique of DC particle sizing via the Coulter Principle. Human peripheral blood granulocyte radius, membrane capacitance, and cytoplasmic conductivity were measured (r=4.1 $\mu$m, $C_{mem}$=0.9 $\mu$F/cm$^2$, $\sigma_{int}$=0.66 S/m) and were found to be consistent with published values.

SUMMARY OF THE INVENTION

It is an object of the present invention to provide a microfabricated alternating current (AC) impedance sensor.

A further object of the invention is to provide microfluidic devices with microelectrodes to enable studies of phenomena at size scales where behavior may be dominated by different mechanisms than at macroscales.

A further object of the invention is to provide microfluidic devices with microelectrodes which are easy to interface to electronic and fluidic interconnect packages that permit reuse of devices, rather than one-time use, crude glue-based methods, useful for electrochemical and biological applications.

Another object of the invention is to provide a microfabricated flow-through impedance characterization system capable of performing AC, multi-frequency measurements on cells and other particles.

Another object of the invention is to provide a microfabricated AC impedance sensor which measures both the resistive and reactive impedance of passing particles, at rates of at least up to 100 particles per second, with an operational bandwidth which approaches at least 10 MHz with a signal-to-noise ratio of at least about 40 dB.

Another object of the invention is to provide a microfabricated AC impedance sensor wherein particle impedance is measured at three or more frequencies simultaneously, enabling the derivation of multiple particle parameters.

Other objects and advantages of the present invention will become apparent from the following description and accompanying drawings. The present invention involves a microfabricated instrument for detecting and identifying cells and other particles based on AC impedance measurements. Two critical elements of the invention are:

1. A glass or polymer-based microfluidic chip, fabricated using photolithographic and chemical etching techniques. Microchannels are etched into one glass substrate, and holes for introducing fluids and making electrical contacts are drilled into a second piece of glass. Platinum or gold electrodes are patterned on both glass substrates, using electrodeposited resist to create features at the bottom of the microchannels. The two pieces of glass are aligned and then fusion bonded using a vacuum hot press or anodically-bonded with an amorphous silicon intermediate layer. Microfabrication is essential for this application in order to make channels and electrodes that are small and precise enough for accurate measurements, and to allow the electrodes to be sufficiently localized to reduce fringing field effects. Using glass reduces parasitic capacitance problems associated with conductive materials such as silicon. Both of these enable multiple AC impedance measurements to be taken on individual particles at high throughput rates.

2. Electrical circuits that connect to the electrodes on the microfluidic chip and detect the signal associated with particles traveling down the microchannels. Two circuits are described: (1) A discrete circuit which relies on the difference in signal between a reference channel with solution only and a measurement channel through which both solution and particles travel. The discrete circuit is capable of measuring impedance changes associated with particles at one frequency, although more than one stage can be used, allowing for measurement at one additional frequency for each additional stage. (2) An integrated circuit which does not require a reference channel and is capable of measuring impedance changes at several frequencies simultaneously. Both of these circuits are capable of detecting a 1% impedance change within the microchannels to 1% accuracy. These circuits enable multiple AC impedance measurements of individual particles at high throughput rates with sufficient resolution to identify different particle and cell types as appropriate for environmental detection and clinical diagnostic applications.

Through work at the Lawrence Livermore National Laboratory developing microfluidic devices for dielectrophoretic separation and sensing of cells and particles, we have fabricated devices from which general or more specialized research devices may be derived. Fluid channels from 80 $\mu$m wide×20 $\mu$m deep to 1 mm wide×200 $\mu$m deep have been fabricated in glass, with lithographically patterned electrodes from 10 to 80 $\mu$m wide on one or both sides of the channels and over topographies tens of microns in height. The devices are designed to easily interface to electronic and fluidic interconnect packages that permit reuse of devices, rather than one-time use, crude glue-based methods.

DETAILED DESCRIPTION OF THE INVENTION

Figure 1:
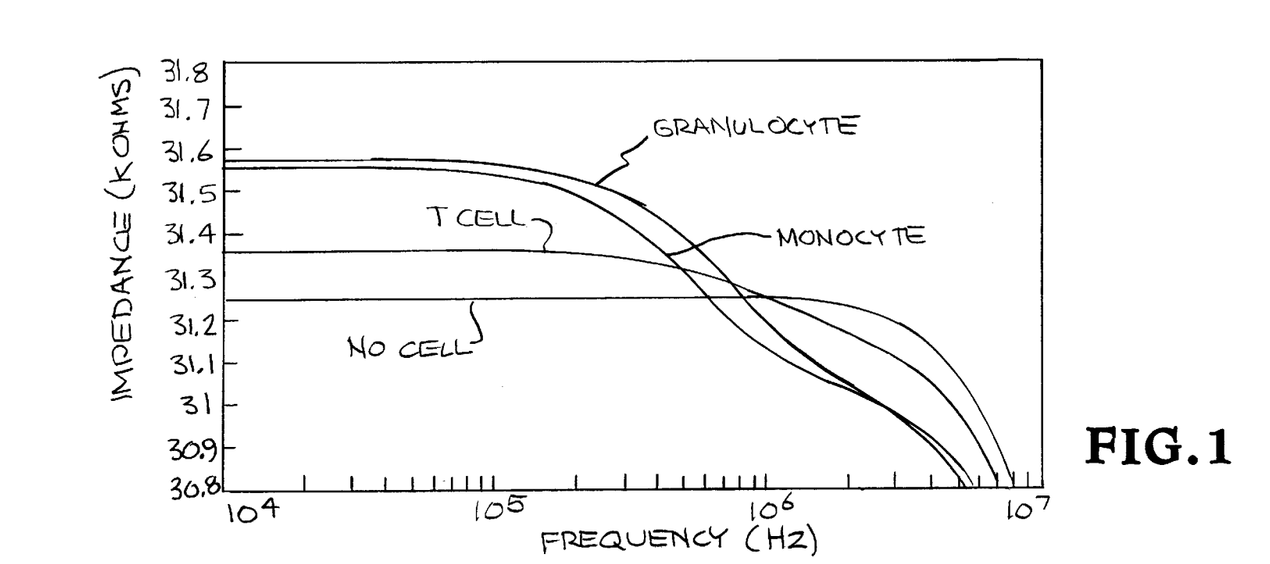
FIG. 1 shows the predicted impedance fingerprint of some different cells, based on cell size and variation in cell membrane properties.

The present invention involves a microfabricated AC device for using in microfluidic systems for electrochemical and biological studies, as well as for use in microfabricated flow-through multi-frequency particle impedance characterization systems. The present invention is directed to a flow-through AC impedance sensor capable of measuring the impedance change in a flow channel due to the presence of a particle at multiple frequencies simultaneously. By measuring the impedance spectrum, or fingerprint, of a cell or particle, it is possible to not only detect its presence, but also determine what type of cell it is. Variations in the dielectric properties of the membranes of different cells result in detectable impedance differences at frequencies up to 10 MHz. The cell membrane is impenetrable to low frequencies down to DC, resulting in impedance changes that are due to displacement of carrier solution and correlate with cell size. Very high frequency signals short circuit the lipid layer of the cell's membrane, exposing elements in the cell's cytoplasm to the field. FIG. 1 shows the predicted impedance fingerprint of some different cells, based on cell size and variation in cell membrane properties.

FIG. 1 illustrates the predicted impedance for 1) no cell, 2) a T cell with a radius = 3.29 μm and $^c mean = 126 \frac{\mu F}{Cm^2}$, 3) a monocyte with a radius = 4.63 μm and $^c mean = 153 \frac{\mu F}{Cm^2}$, and 4) a granulocyte with a radius = 4.71 μm and $^c mean = 1.10 \frac{\mu m}{Cm^2}$, where $^c$mean=membrane capacitance, and F=Farads, a unit of capacitance.

The ability to differentiate between different cells and particles has several applications:

1. Differential blood cell analysis—determining the relative populations of different cells within a sample. This can be used for disease diagnosis.
2. Detection of abnormal cells, and determination of cell state.
3. Immunosensing when used with antibody-coated beads.
4. Sample preparation—cells or other biological particles such as spores, can be separated from non-biologicals, such as dirt, as a screening step after sample collection and before sample analysis using an assay such as PCR or flow cytometry.

Because the system described herein uses microfabrication technology and because it is based strictly on impedance measurements, it is possible to make miniature, robust systems suitable for testing in the field. Optics-based flow cytometry is a pervasive bioanalytical tool used for cell counting and identification, as well as for immunosensing. These instruments are commonly found in diagnostic laboratories at hospitals and at biological research facilities. Due to complex optics systems and extreme alignment sensitivity, miniature, portable optics-based cytometers are not feasible. The invention will enable development of a robust, portable, inexpensive bioanalytical instrument capable of real-time identification and analysis of cells based on impedance measurements. This instrument would have major implications on health care in remote and underprivileged areas. A flow cytometer system based on a microfabricated chip and built-in electronics rather than bulky optical components to probe the cells could easily be developed into a hand-held unit.

Two key technologies enable this invention: a microfabricated fluidic sensor chip, and custom-designed circuitry. The combination of these two technologies results in a well-controlled/well structured sensor geometry, low noise, higher sensitivity, and the flexibility to use with nonphysiological ion strength solutions. The microfabrication process used to make the microfluidic devices is described hereinafter. Additional aspects of the device include:

1. Glass is an essential substrate material because it mitigates problems with parasitic capacitance. Plastic or another non-conductive material could be used as well.
2. The sensor geometry was optimized for high sensitivity and low parasitic capacitance.
3. Grounding electrodes are patterned within the flow channels to reduce noise.
4. The electrodes have been designed to increase field uniformity and improve sensitivity.
5. Hydrodynamic focusing within the channels helps center particles, moving them away from fringing fields near the edge of the electrodes.
6. Platinum (approximately 0.1–0.2 microns thick) with a thin chromium adhesion layer (approximately 0.5 nm thick) is optimum for long-lasting electrodes. Ti/Au is a suitable lift-off layer for patterning the Pt electrodes.

By comparison to existing approaches, the AC impedance measurement yields far more information than DC Coulter-counting regarding cell electric properties, in this case, membrane dielectric capacitance and conductance of cells. These properties are different for different cells, thus the apparatus can be used to count, discriminate, analyze and characterize cell mixture populations. It can also be used as a "dielectric spectrometer" to measure the frequency-dependent cell dielectric properties.

Figure 2:
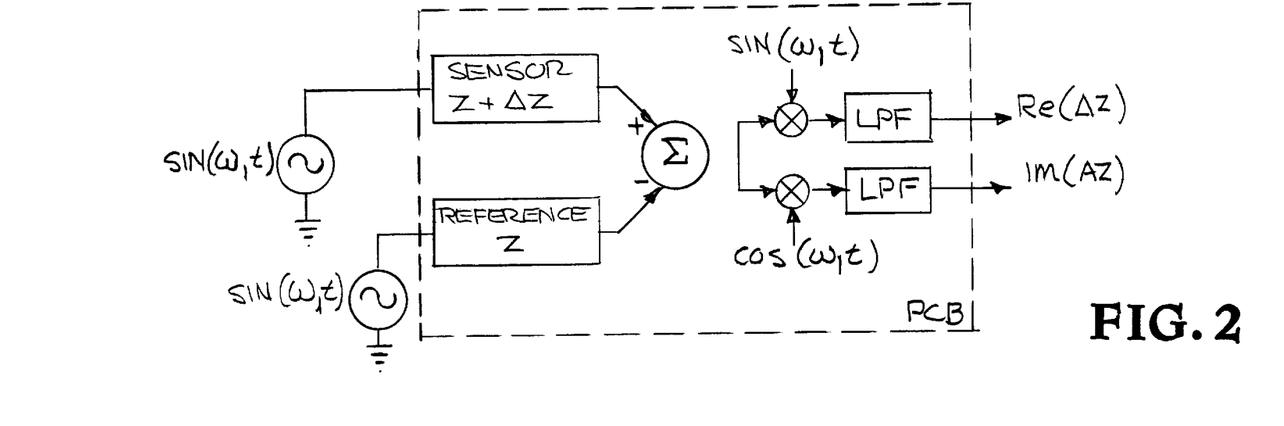
FIG. 2 illustrates an embodiment of a circuit for detecting the impedance change associated with a particle passing between the electrodes in the microchannel, and which uses standard components mounted on a printed circuit (PC) board.
Figure 3:
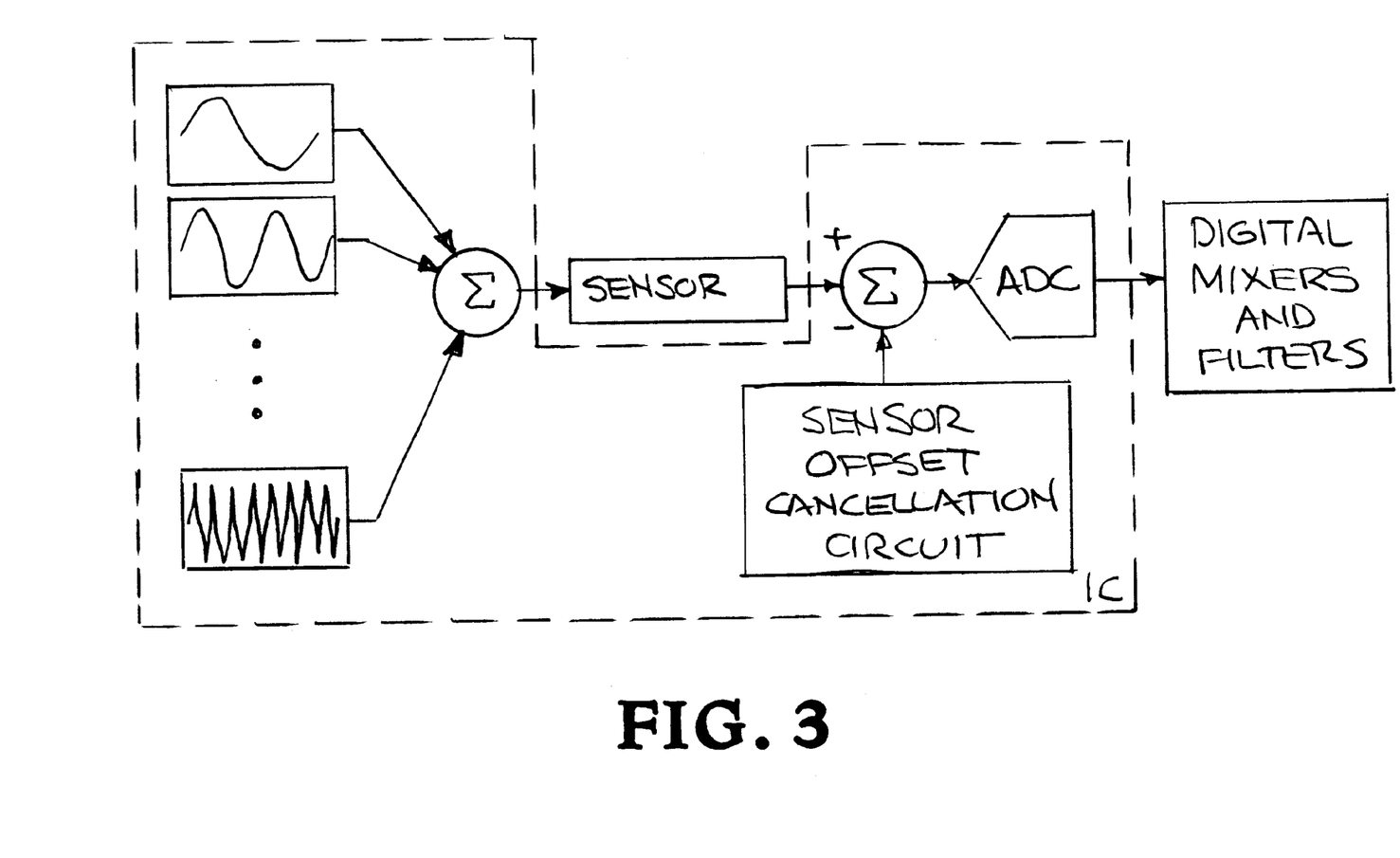
FIG. 3 illustrates another embodiment of a circuit for detecting impedance change which comprises a custom integrated chip (IC), and can measure several frequencies simultaneously and eliminates the need for a reference channel, as in the FIG. 2 circuit.

Two circuits have been developed for detecting the impedance change associated with a particle passing between the electrodes in the microchannel. One illustrated in FIG. 2 uses standard components mounted on a PC board, which we refer to as the discrete circuit. The second, illustrated in FIG. 3, incorporates a custom integrated chip which we refer to as the integrated circuit. The main advantages of the integrated circuit are that it can measure several frequencies simultaneously, and it eliminates the need for a reference channel, which is required by the discrete circuit. The discrete circuit can measure more than one frequency at a time, but requires additional stages for each additional measurement frequency.

Figure 4:
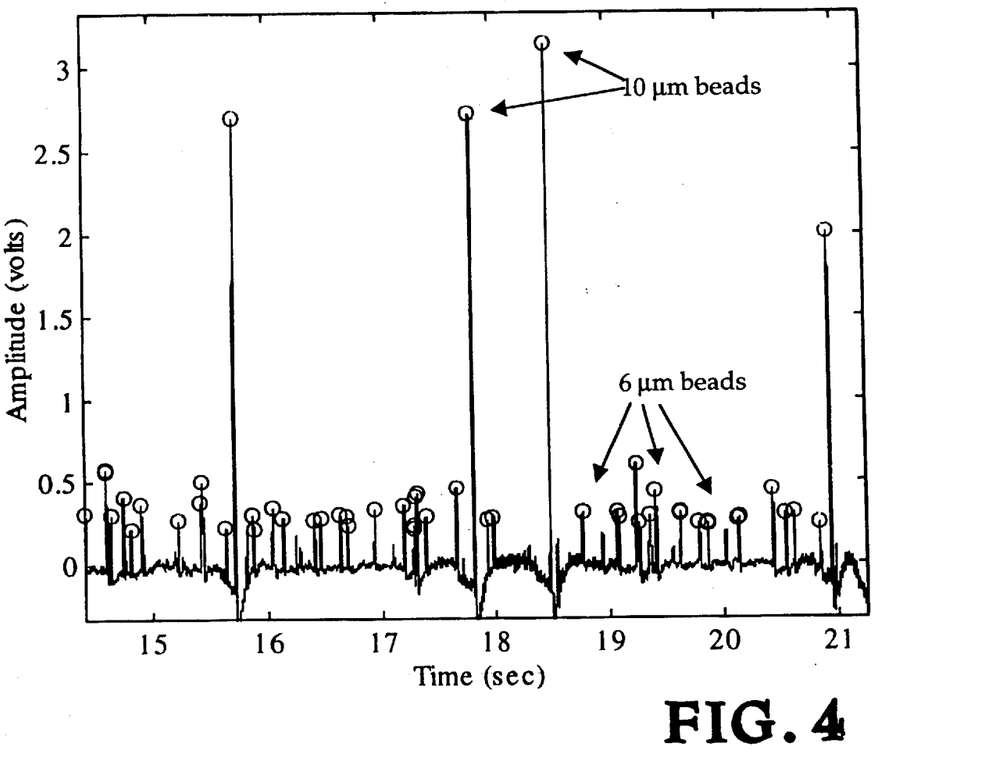
FIG. 4 illustrates the test results of a first generation impedance sensor using the circuit of FIG. 2 at 1 MHz with a mixture of ten and six micron beads in the microchannel.

We tested the first generation impedance sensor using the discrete circuit at 1 MHz with a mixture of ten and six micron beads. The results, shown in FIG. 4 with circles denoting picked peaks, indicate that we can easily distinguish between these two bead types—the tall peaks correspond to ten micron beads, and the smaller peaks are the six micron beads, with signals well above the noise floor. To distinguish between certain cell types, we must be able to resolve 1% impedance variations.

Recent efforts have been directed to forming smooth surface microchannels to prevent channel cross-sections having sharp corners to prevent trapping of particles in those sharp corners. These efforts are directed to forming microchannels with circular cross-sections. One approach involves isotopically etching a channel into a glass substrate, fusion bonding a glass substrate over the formed channel, and annealing the glass which transforms the channel cross-section to a circle. Another approach involves etching a channel into a glass substrate, forming a layer of silicon on the channel surface, forming a layer of wax on the silicon layer, bonding a second plate over the wax, annealing whereby a circular channel is formed, and thereafter removing the wax.

As pointed out above, microfabrication has become an enabling technology for development of the next generation of analytical instrumentation for performing medical diagnoses, sequencing the human genome, detecting air borne pathogens, and increasing throughput for combinatorial chemistry and drug discovery. These miniature devices take advantage of scaling laws and unique physical phenomena which occur at the micro-scale to perform new types of assays. The large surface area to volume ratio and small size of microfabricated fluidic devices results in laminar flows, increased surface contact between sample fluids and electrodes, fast and uniform heat transfer, and reduced reagent use. Surface tension and viscous forces dominate while inertial effects are negligible. Microfabricated electrodes can produce high electric fields for electroosmotic flows and electrophoretic separations, and large field gradients for inducing dielectrophoretic forces on particles.

Microfabrication technology for producing microchannels with embedded electrodes which make contact with the working fluid is described in a paper by H. Ackler et al., "Microfluidic Systems For Electrochemical and Biological Studies," Proc. 194$^{th}$ Meeting, Electrochemical Society, Boston (1998) 54. The following description of the microfabrication technology for producing the microfabricated AC impedance sensor includes portions of the above-referenced paper.

Devices with channels between 20 and 200 $\mu$m deep have been fabricated using isotropic glass etching and fusion bonding. Gold or platinum electrodes can be patterned on the bottom and/or top of the channels for various applications. Advantages of the process include hermetically sealed channels and electrodes, transparent substrates for easy visualization, large variability of channel depth even on the same device, and electrical and fluid contacts on the same side of the microfluidic chip to enable surface mounting. The first devices fabricated using this process were a particle separator and an AC impedance sensor. The separator has a 200 $\mu$m deep channel with interdigitated electrodes at the channel's bottom surface. An AC field across the electrodes induces a dielectrophoretic force on particles within the channel, levitating different particles to equilibrium heights determined by their size and dielectric properties. The parabolic velocity profile associated with laminar flow from an external pressure source results in separation of an injected sample of particles as they are carried down the channel. This separation technique, referred to as DEP/FFF for dielectrophoresis combined with field flow fractionation, was demonstrated recently using large area photolithographically-patterned planar electrodes on flat glass substrates. The AC impedance sensor device has 20 $\mu$m deep channels with opposed electrodes for detecting and identifying particles as they flow by.

In addition to these examples, the fabrication process can be used for making integrated devices suitable for performing electrophoretic separations, electroosmotic pumping, flow sensing, and trapping desired species from a larger sample for subsequent processing or analysis. Examples of the latter include patterned electrodes used to capture and hold both DNA and spores. An AC signal is applied between adjacent electrodes, creating large gradients in electric field near their edges. The biological material is captured in such areas of high field strength by dielectrophoretic forces. The 50 $\mu$m wide by 2000 Å thick Ti/Pt electrodes with 30 $\mu$m gaps were patterned on glass using processes discussed below. When the electrodes are deenergized, the captured species may be moved to other sections of the device for further processing or analysis. Clearly, numerous other phenomena may be studied with devices fabricated by these methods.

The microfluidic devices described hereinafter are typically fabricated by patterning fluid channels and electrodes on the surfaces of glass (Pyrex) or silicon substrates. The substrates are bonded together, thereby sealing the channels and electrodes within a bulk piece of material which is then diced to give discrete devices. Fluidic and electronic interfacing is accomplished through holes drilled through one of the substrates. Fabrication may be categorized into the etching of fluid channels, patterning of electrodes, and bonding which are discussed separately below.

Fabrication:

There are two ways to bond the glass substrates:
1. Hot Press, and
2. Anodic Bond.

Figure 5:
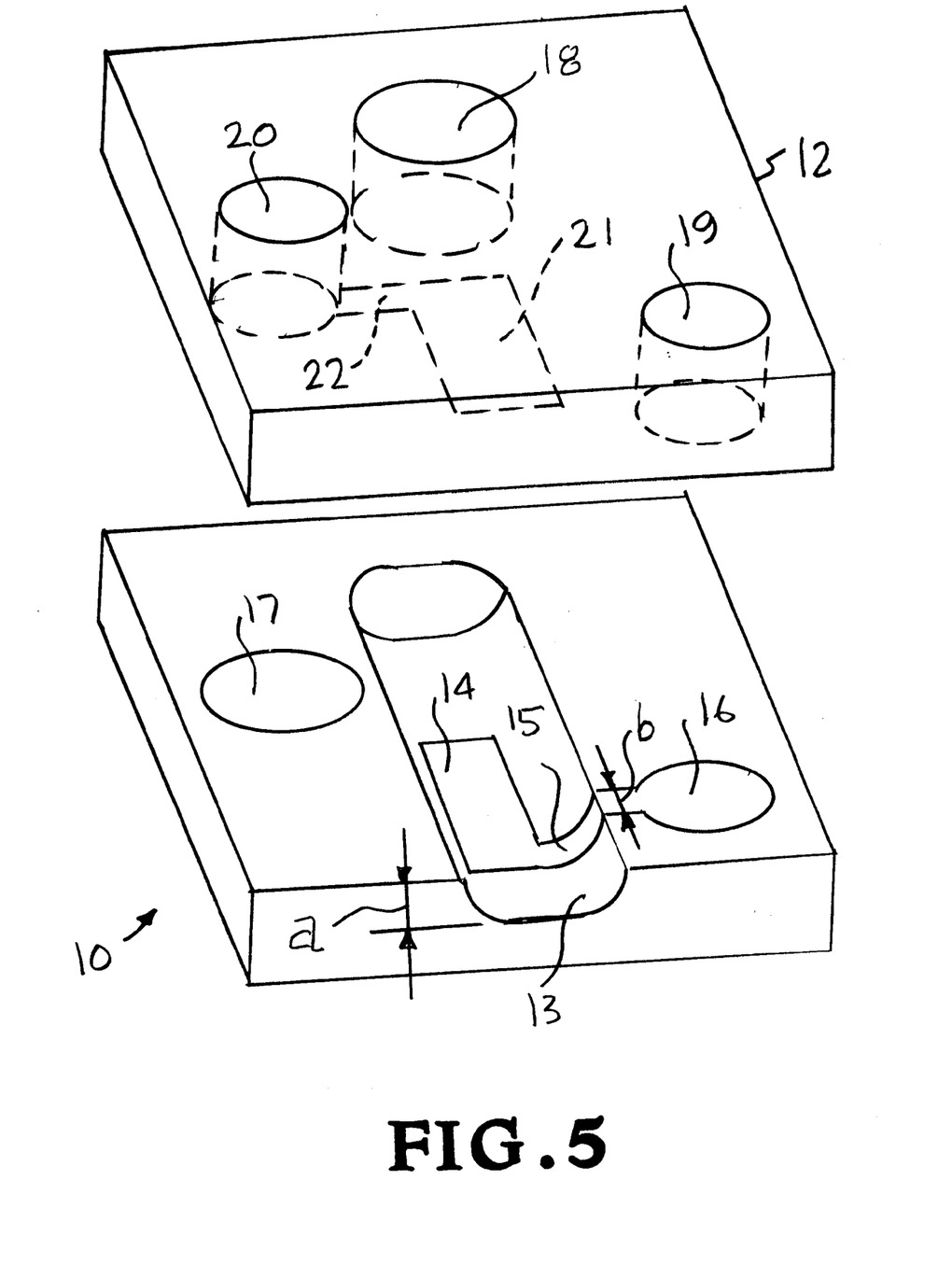
FIG. 5 is an enlarged exploded view of an early embodiment of an AC impedance sensor glass chip made in accordance with the present invention, illustrating a microchannel with patterned electrodes and fluidic and electronic feedthroughs on one side of the chip.

Channel Etching:

The fabrication of microchannels in glass begins with cleaning the glass surface with a cleanroom soap solution. The surface is then coated with a metallic glass etch mask layer consisting of a 30 nm chromium bond layer and 200 Å-1 $\mu$m of gold on top of it, which is then patterned with photoresist lithographically. The metals are etched through the photoresist windows, forming the pattern through which the glass is etched with a 22 vol. % HF/78 vol. % Acetic Acid solution. The etch rate is about 0.7 $\mu$m/min. The photoresist and etch mask are then stripped from the substrate. A typical microchannel pattern is shown in FIG. 5. This channel is etched approximately isotropically. The initial etch mask was 50 $\mu$m wide. The etch depth is 40 $\mu$m, the channel width at the top is 120 $\mu$m, and the undercut of the glass channel top edge is about 50 $\mu$m. The surface roughness measured with a stylus profilometer was 20 nm in the bottom of the 40 $\mu$m deep etch regions and 2 nm in the masked top surface nearby. The overhanging lip or cornice at the edge influences the final microchannel cross sectional shape, rounding corners at the sides when bonded to the other substrate. This may be important for fluid flow dynamics, ease of cleaning and flushing, and preventing trapping of particles. If the cornice is not desired, it may be rounded off by a brief glass etch over the whole substrate, subsequent to removing the metal etch mask. This must be done if electrodes are to be patterned into channels. Otherwise, the overhanging cornice of glass will prevent the deposition of a continuous metal line into the channel. After etch to round corners, add (deposit) amorphous Si or glass. Deposition of amorphous Si is done on the thicker piece of glass at a temperature of 550° C. Deposition time is 18 mins. Lay glass on flat piece of silicon to avoid warping of glass. Additional channels of other depths can be etched by repeating the proun to the same substrate, using an electrodeposited rant to ev enly coat the etched substrate.

Electrode Patterning:

While patterning electrodes photolithographically on planar surfaces is trivial, doing so over topographies tens of microns in height is quite difficult. The patterning of electrodes along channel sidewalls and near drilled holes is extremely difficult with conventional photoresist and lithographic processes. The steep sides of the channels make it virtually impossible to get good step coverage with spin coated photoresist. Capillary forces cause photoresist to flow to regions of negative curvature (into channels) and toward the edges of drilled holes, resulting in resist thickness varying by up to an order of magnitude. Such large variations in resist thickness make proper exposure and development of any pattern across a substrate a hopeless endeavor. In order to overcome this inherent problem with spin-on resist, a process was developed using a negative-working anodic electrodeposited photoresist (NEPR, Shipley Eagle 2100), which was originally developed for the printed circuit board (PCB) industry as a replacement for dry film resist. Photoresist films deposited electrochemically tend to coat even the most severe topographical features very uniformly. The NEPR is an aqueous mixture consisting of the various components of a typical negative resist (minus the xylene solvent) emulsified in water. The micelles which result from the emulsification are positively charged, and migrate to a negative electrode (the part to be coated) in the presence of a strong electric field. The micelles are destabilized at the electrode, and consequently, are deposited there. In order to deposit NEPR, the surface must be reasonably conductive, so the process is well suited to metal etching or plating. Prior to resist deposition, a metal film (copper, nickel, gold, or platinum) is typically deposited onto the part to form the conductive layer. A potential of 50–100 volts is applied between the part to be coated and a counter electrode of comparable size. Resist deposition takes less than a minute, and is fairly self-limiting (i.e., the "electrode" becomes an insulator as the resist film builds up). Typical resist thicknesses range from 5 to 12 microns, and can be varied with plasticizer content or temperature variation. The resultant film is rinsed with water and soft baked, or left to air dry.

The resist film can be exposed with conventional lithographic tools. A UV dose of 150–300 mJ/cm 2 at wavelengths between 300 and 400 nm is sufficient to expose the resist. A dilute solution of lactic acid is used to develop the latent pattern. After metal etching, the resist can be removed with concentrated lactic acid, or with polar aprotic organic solvents.

The ease with which chromium and gold may be wet etched makes these metals desirable for electrodes on glass or silicon, using a very thin film of the former as a bond layer and a thicker film of the latter for the electrode surface. The electrodeposited resist may then be deposited onto the gold surface, conformally over the edges of channels and drilled holes, then photolithographically patterned. The underlying gold and chromium films are then wet etched, and the resist stripped. For surfaces in contact with the photomask (i.e., zero gap between mask and substrate), line widths down to 10 $\mu$m are reproducibly achieved. Electrodes patterned into 20–25 $\mu$m deep channels are typically broadened by 2–5 $\mu$m. An AC impedance sensor has been fabricated with 60 $\mu$m×80 $\mu$m Cr/Au electrodes, one in the bottom of a 20 $\mu$m deep channel and the other on top. These electrodes form the capacitor used for an AC impedance sensor and 20 $\mu$m metal lines connect them to large electronic contact pads approximately 1 mm from the channel.

For some environments, platinum electrodes may be preferred, but platinum is extremely difficult to etch. Therefore the direct metal patterning method above is not suitable for fabricating Pt electrodes. However, the electrodeposited resist still requires some sort of metal layer over the entire surface. We have developed a lift-off process wherein a Ti/Au layer is deposited on the substrate and used for deposition of the resist. The resist is used to pattern features into the Ti/Au layer, through which Cr/Pt electrodes may be deposited (Cr is used for the bond layer). The resist and Ti/Au is then dissolved from under the unwanted portions of the Cr/Pt film which is washed away, leaving the desired Cr/Pt electrodes. This method has been demonstrated to produce electrodes in channels that are as good as directly patterned Ti/Au.

Bonding:

To complete the devices, a matched pair of substrates must be precisely aligned using lithographically patterned metal alignment markers and bonded together. Anodic bond of glass to glass is carried out at a temperature of 550° C. ramp oven over a 2.5 hour period. Induce HV ramp to 1000V. Anneal for one hour at 550° C. and cool overnight or about 3 hour ramp down. Fusion bonding of the substrates, wherein the mated surfaces are pressed together at elevated temperatures, has been found to work very reliably. However, the bonding of substrates to form sealed channels is a balance of conflicting needs. High temperatures, pressures, and long bond times improve bond strength and conformal sealing of glass around electrodes, and reduce voids and other defects at the bond interface. However, if the temperature and pressure are too high, or the bond time too long, deformation of the glass may cause the faces of channels parallel to the substrates to be bowed toward each other. The most dramatic case of this results in the opposing faces coming into contact and bonding, closing off the channel. Hence, bonding process variables are determined by the dimensions of the channels. We have determined that temperatures 150–200° below the softening point of the glass, pressures around 5–10 MPa, and times at maximum temperature and pressure of a few hours are suitable for most devices. This method of bonding has also been found to be useful for joining glass and silicon surfaces. After bonding saw into pieces of desired sizes.

Detailed Process Flow:

1. Clean Glass.

Turn on Breaker #10 for hot water.

Flush parts with soapy water.

With very soapy cloth break edges and then rinse well.

New soapy cloth clean surface and rinse well 10 mins.

Always change gloves. Dry on rack start at top and work way down.

Glass with holes drilled, pretreat with etch in HF for 1 min.

2. Sputter deposit Masking metal on both sides of glass. (Perk & Elmer) Thin glass 1.1 mm and Thick glass.

200 A—Cr

2000 A—Au

Make sure Crome is lit.

3. Pattern Channels (Thick glass).

Dip coat with SP 2029 resist.

Bake at 90C for 45 mins. to 1 hour.

Mask: 200 Channel.

Expose 1050 mj.

Develop developer 203A 2.5 min.

Inspect.

No Hard bake.

Plasma ash 1 min. 300W.

Pattern channels (Thin glass with holes).

Deposit electroplated resist Eagle 2100.

Wet surface.

27C, 75 W, for 15 sec.

Let stand in Nitrigon chamber for 24 hrs.

Mask: 20 channel.

Expose 200 mj.

4. Etch Metals.

Au Etch for 2 mins. or until clear.

Cr etch EDTA 5 mins until clear.

Inspect.

5. Channel Etch.

Measure resist thickness for start point.

22% HF to 78% Acetic acid at room temp. low stir #2

Hold vertical with spinner.

Etch about 10 mins. Cover alignment marks with black wax. Then continue etching.

Etch rate 0.9 microns per min.

Etch depth.

Check etch rate.

Strip resist, Au and Cr.

Inspect channels.

Thin glass etch 20 microns deep.

Thick glass 200 micron deep.

6. Round Channel edge. Do not forget this step!!!

HF dip 8 mins.

Deposit Amorphous Si on Thick Glass.

Set heaters at 550-157-525 for 550C.
Deposition time 18 mins.
Lay flat on Si piece cut to lay on boat.
7. Deposit Ti Au for Electroplated Resist.
150 A of Ti (5 A per min.).
5000 A of Au (5 A per min.).
Channel side only.
8. Electroplated Resist.
Eagle 2100 photoresist.
Heat to 27c for 11000 a resist.
Temp. dependent varies each batch do a sample piece each time.
(Bake sample 10 mins. 90C then measure for thickness).
9. Dry Photoresist. Do not bake it Topographical (3D).
Place in N2 desicator for at least 24 hours or until not tacky.
If Planar Features soft bake at 90C for 10 mins.
10. Expose.
Use Big Flood source for thick plates.
Use QEV for 1.1 mm glass no hard contact-Proximity make sure.
QEV UV power is close to 15 mj. If not cracking will take place.
Expose 200 mj time depends on lamp.
Shipley specifies an exposure of 150–300 mj/cm2 for a 30 mu film.
11. Develop.
Use Eagle developer at 37° C. for 2–2.5 mins.
Rinse, dry, and inspect.
Plasma Ash 3×50 w for 3 mins. with 5 min. cool in between runs.
If developer is too hot, it will strip resist.
Develop whole plate undeveloped resist will do strange things in E-beam if not developed.
12. Metal Etch.
Etch gold.
Etch Ti.
Rinse well and dry.
UV Stabilization for photoresist!!!
Flood expose 500 mj.
13. Deposit Cr/Pt for lift-off.
Use EB-2 Planetary. Let pump over night for good adhesion.
Cr-150 A 2A per sec.
Pt-1000 A 2A per sec.
14. Metal Lift-off.
Soak plate in Acetone and ultra-sonic bath until Ti—Pt lifts off.
Clean with Acetone and IPA.
Plasma Descum 5 mins. 300 w.
To clean residue from Photoresist may need to do a light paranha.
H2S04 200 ml: H202 75 ml let cool 10 mins then 10 sec dip.
15. Etch Ti—Au.
Etch back Gold.
Etch back Ti.
Inspect plate.
Paranha etch will strip Ti and Pt.
16. Pre-clean for bond.
Light paranha. H2S04 200 ml: H202 75 ml let cool 10 mins. then dip for 10 sec.
17. Alignment for bond.
Align Top and Bottom plates using Quitel aligner.
Use binder clips to hold in place.
Anodic Bond.
550C 2.5 hour ramp.
Bond about one hour. Anneal for one hour. Cool over 3 hours.
Saw into devices.

Device Packaging:

While the ability to fabricate micron-scale mechanical and fluidic structures out of silicon, glass, and plastic is advancing rapidly, one of the main difficulties continues to be interfacing these microfabricated devices to each other and to the outside, macroscopic world. Introducing fluid samples and reagents into microfluidic devices is challenging, especially when multiple inputs are required. Many microfluidic systems utilize epoxy for their connection schemes, which is permanent, can cause channel clogging, is not mechanically robust, uses excessive area, and requires extensive manual assembly time. Microfluidic packaging developed at Lawrence Livermore National Laboratory (LLNL) does not require adhesives to make connections and provides quick and easy exchange of microfabricated components. Furthermore, the connectors have a low dead volume, are helium leak tight, can withstand high pressures, and have a small footprint, allowing for multiple connections to be made in a very small area, thereby retaining the advantages of miniaturization.

The miniature connector developed at LLNL enables introduction of microliter and sub-microliter quantities of solutions into microfabricated fluidic devices and provides a means for interconnecting various microfluidic devices to each other. The connector joins standard high pressure liquid chromatography (HPLC) PEEK tubing to the bonded glass microfluidic devices. The tubing end mates with the fluid inlet/outlet ports in the microfluidic chip (see FIG. 5). The chip is held against a substrate, in this case the backside of a printed circuit board with through holes for the tubing, using custom machined support plates. The PCB is backed by another plate through which the tubing also passes. The tubing is held in place with machined hollow screws which press a ferrule and o-ring onto the tubing end, forming the seal against the chip surface around the inlet/outlet ports. Electronic connection is made between the electronic contact pads on the chip (round pads in FIG. 5) and pads on the PCB with a conductive elastomer which is placed into the electronic feedthrough holes in the chip. The elastomer is compressed when the support plates are clamped together, thereby insuring good electrical contact. The connector has been used extensively with excellent results, allowing for easy and effective exchange of microfluidic devices and the introduction of different solutions into microfluidic devices. The package also allows for electronic connection between devices and standard electronic cables for interfacing to computers or other electronic instruments.

Referring now to FIG. 5, the microfluidic device is provided with connector ports for external fluid and electrical connection, which are formed in the glass plates of the device. As shown, the device generally indicated at 10 includes a bottom glass or plate 11 and a top glass or plate 12. Bottom glass 11 includes a microchannel 13 having a depth indicated by arrow a of 20 $\mu$m, for example, a sensor electrode 14 formed in the bottom of the microchannel 13 and connected by lead 15, having a width indicated by arrow b of 10 μm, for example, to an electrical contact pad 16, formed on the upper surface of bottom glass 11. Another electrical contact pad 17 is formed on the upper surface bottom glass 10 on a side of microchannel 13 opposite pad 16. Top glass 12 is provided with drilled holes 18,19 and 20, (not all holes shown) and an electrode 21 with lead 22 is formed on the bottom surface of top glass 12. Drilled hole 18 comprises a fluid inlet/outlet, while drilled holes 19 and 20 each comprise an electronic feedthrough and are located over pads 16 and 17 when top glass 12 is bonded to bottom glass 11, with electrode 21 located in spaced relation to electrode 14, lead 22 in contact with pad 17, and fluid inlet/outlet being in communication with microchannel 13.

Microfluidic devices with suitably incorporated microelectrodes have been demonstrated to be practical for conducting standard processing and analytic biological and electrochemical procedures. Perhaps more importantly, they are also an enabling technology for conducting such procedures in a highly parallel fashion, at smaller scales, and for conducting new investigations and procedures that previously may not have been practical with macroscale instruments. There is great promise for miniature deployable microfluidic systems which monitor the environment for toxicants and biological species, and hand-held medical diagnostic instruments incorporating microfluidic chips. Devices fabricated at LLNL, for example, have been demonstrated to meet these goals which, when packaged with sample preparation and control systems, will be about the size of a typical lunch box. The compactness of such devices makes them very affordable and portable. With the convenience of portable computers, they become highly suitable for research or clinical tests in the field or lab.

See C. K. Fuller, "Microfabricated Multi-Frequency Particle Impedance Characterization System," presented at Micro Total Analysis Systems 2000, May 14–18, Enschede, the Netherlands.

In addition, we have developed a microfabricated flow-through impedance characterization system capable of performing AC, multi-frequency measurements on cells and other particles. The sensor prototype measured both the resistive and reactive impedance of passing particles, at rates of up to at least 100 particles per second. Its operational bandwidth approached 10 MHz with a signal-to-noise ratio of at least approximately 40 dB. Particle impedance is measured at three or more frequencies simultaneously, enabling the derivation of multiple particle parameters. This constitutes an improvement to the well-established technique of DC particle sizing via the Coulter Principle. Human peripheral blood granulocyte radius, membrane capacitance, and cytoplasmic conductivity were measured (r=4.1 μm, $C_{mem}$=0.9 μF/cm$^2$, $\sigma_{int}$=0.66 S/m) and were found to be consistent with published values.

The system described hereinafter combines the advantages of microfabrication technology (low cost, scalability, and size) with a new circuit architecture and high-speed data processing to overcome the limitations of existing impedance characterization schemes. It consists of a microfabricated device with two identical microchannel sensors: one channel for sensing particles as they flow through the device and the other for use as an electrical reference. The microfluidic chip is mounted on a circuit board containing electronics that simultaneously measure resistive and reactive changes in the differential impedance of the microchannel sensors. The system operates at multiple, software programmable frequencies from 100 kHz to 10 MHz and can accommodate solution conductivities of between 50 and 250 mS/m. Unique packaging allows the sensor, circuit board, and fluidic interconnects to be assembled easily and within a small footprint.

Figure 6:
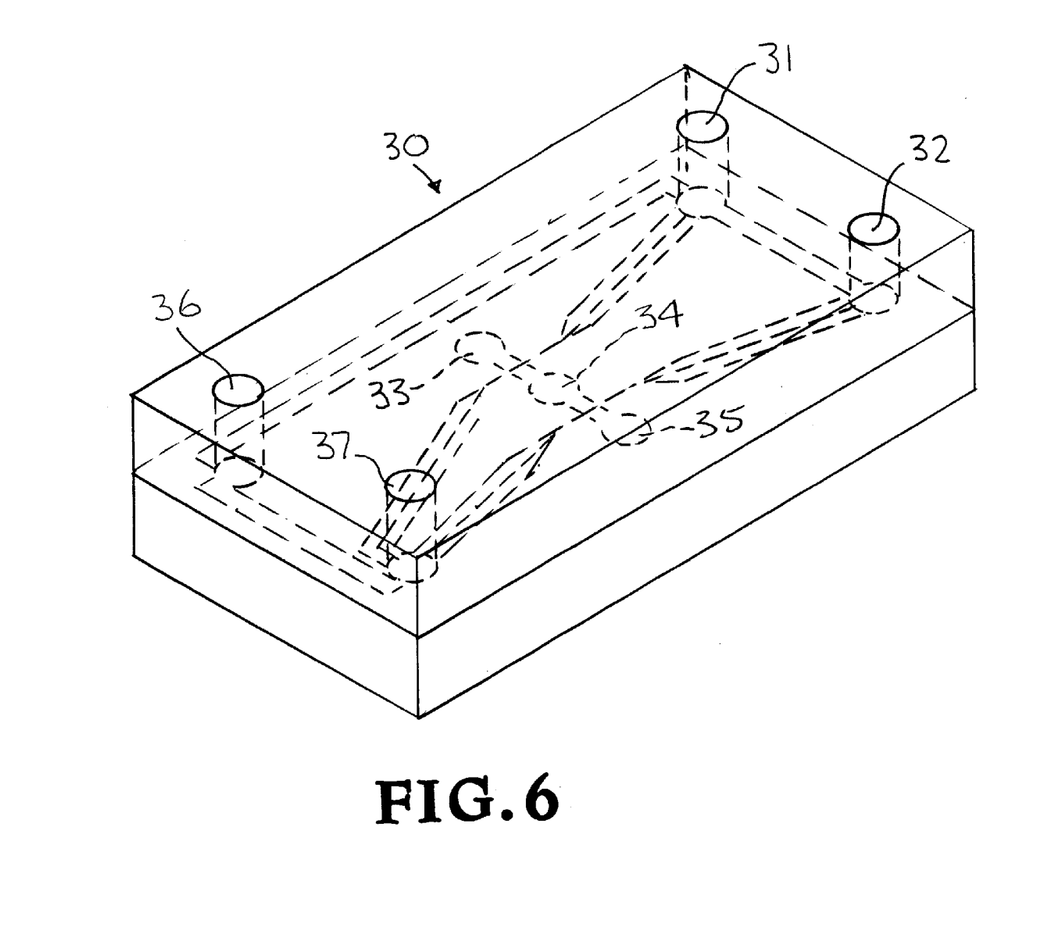
FIG. 6 illustrates a 9×16×4 $mm^3$ AC impedance sensor chip illustrating both the sense and reference channels formed using microfabrication and custom-designed circuitry for microfluidic devices.
Figure 7:
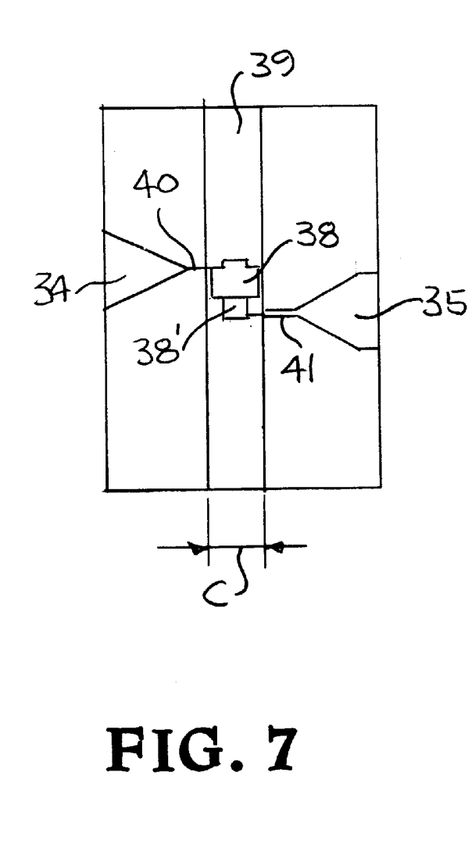
FIG. 7 is a greatly enlarged view of a microfabricated channel and parallel plate sensor electrodes of the FIG. 6 sensor chip.

FIG. 6 illustrates an embodiment of the identical dual microchannel sensors and FIG. 7 is a greatly enlarged view of the microfabricated channel and parallel plate sensor electrode of FIG. 6. By way of example the impedance sensor chip of FIG. 6 is of a size 9×16×4 mm$^3$, with the sensor electrode of FIG. 7 having a width of 80 μm. As shown, the FIG. 6 sensor generally indicated at 30 has a sample input 31, a reference input 32 at ends of two channels, three electrode contacts 33, 34 and 35, a fluid ground contact 36 electrically connected to sample inlet 31, and a fluid outlet 37 connected to each channel. FIG. 7 illustrates electrodes 38 and 38' formed in a microchannel 39 having a width of 80 μm as indicated by arrow c and connected by leads 40 and 41 respectively to pads or contacts 34 and 35 of FIG. 6.

Mircofabrication techniques enable the construction of specific sensor geometries which maximize the operational bandwidth by reducing the effects of the sensor's parallel plate and double-layer capacitances. The microchannels are isotropically etched 20 μm into a glass substrate, and electrodeposited photoresist is used in a lift-off process to define 3D platinum electrodes in the channel bottoms. The opposing electrodes are patterned onto a second glass substrate that is ultrasonically drilled to produce electrical and fluidic vias. These two glass plates are aligned and bonded, sealing the electrodes inside the channels. The resulting active sensing region is approximately 70 μm wide and 70 μm long with 20 μm of separation between the electrodes.

The system uses a homodyne circuit architecture which mixes the resistive and reactive components of particle impedance to DC for detection. It accommodates various operating conditions and measurement frequencies with a simple gain adjustment; the tuning of individual frequency channels is not required. Moreover, system and sensor-induced gain and phase shifts are easily normalized using polystyrene calibration beads. During testing, particles suspended in the carrier solution flow through the sense microchannel, while particle-free carrier solution flows through the reference channel. The sense and reference electrode sets are driven out of phase using a signal formed from a summation of the measurement frequencies. The currents through each electrode set are combined, amplified, mixed, filtered, digitized, and transferred to a computer for analysis. As particles enter the sensor region, the computer stores the maximum changes in the difference currents for the in-phase and quadrature-phase components at each frequency. These changes are proportional to the real and imaginary parts of the particle's impedance, from which the desired parameters are derived.

The first system prototype uses discrete mixers, filters, and direct digital signal synthesis circuitry to measure complex impedance at three frequencies, and it achieves a signal to noise ratio (SNR) of approximately 40 dB. A mixed digital and analog application-specific integrated circuit (ASIC) that will expand the number of possible simultaneous measurement frequencies to eight and improve the SNR has been fabricated and is undergoing testing. Eight frequencies will enable the use of more complex particle models and allow conclusions to be drawn about additional particle parameters, including cell membrane conductivity and internal permittivity (which reflects endoplasmic reticulum and nuclear structure). For both systems, the maximum measurement rate is limited by the analysis software to less than one hundred particles per second, but by incorporating the peak picking and filtering algorithms in hardware, measurement rates exceeding one thousand particles per second are readily attainable.

Figure 8:
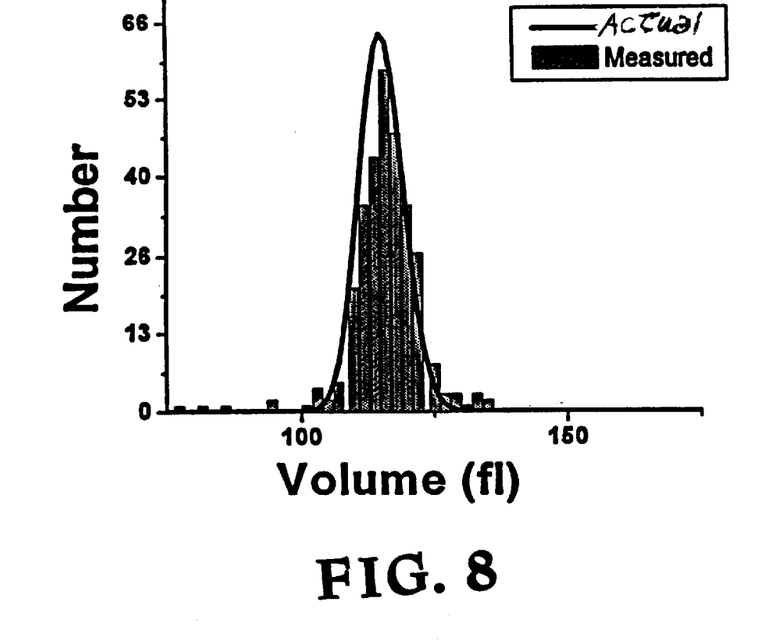
FIG. 8 illustrates the actual and measured volume distribution for calibration beads for the sensor of FIG. 6.

Initial device testing revealed differences in the measured and expected volume distributions of calibration beads. This discrepancy was attributed to the settling of beads in the microchannel; at low flow rates the beads fall from suspension and encounter the fringing field at the edge of the sensor electrode. For flow rates in excess of 1 ml/hr, hydrodynamic focusing positions the particles towards the channel's center, away from the inhomogeneous field, and the measured particle sizes closely match the predicted distribution based on the manufacturer's specifications (FIG. 8).

Figure 9:
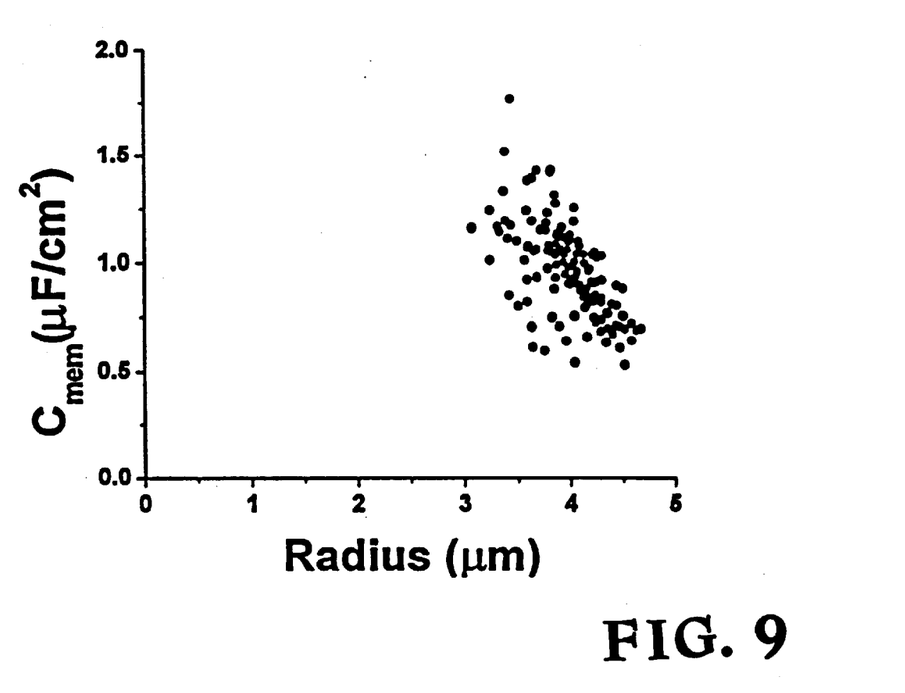
FIG. 9 illustrates cellular parameters derived from preliminary measurements using the sensor of FIG. 6.

Preliminary tests using human peripheral blood granulocytes in a 50 mS/m buffer solution are shown in FIG. 9. The mean radius of 4.1 $\mu$m, membrane capacitance of 0.9 $\mu$F/cm$^2$, and cytoplasmic conductivity of 0.66 S/m derived from impedance measurements compare favorably with accepted mean values from ROT experiments (r=4.7 $\mu$m and $C_{mem}$=1.1 $\mu$F/cm$^2$, $\sigma_{int}$=0.60 S/m). In addition, the system successfully measured the expected difference in cytoplasmic conductivity between paraformaldehyde fixed and unfixed granulocytes.

A system using the sensor of FIG. 6 has been demonstrated that accurately measures resistive and reactive particle impedance in a flow-through system. Its wide bandwidth and easily adjustable operating frequencies enable characterizations of various particle types under different operating conditions. The volume, cytoplasmic conductivity, and membrane capacitance of human peripheral blood granulocytes were successfully measured. It is anticipated that this system will be capable of differentiating subpopulations of cells and biological particles that are indistinguishable with existing flow-through electrical particle characterization techniques.

It has thus been shown that the present invention provides a microfabricated flow-through AC impedance sensor capable of measuring the impedance change in a flow channel due to the presence of a particle at multiple frequencies simultaneously. By measuring the impedance spectrum, or fingerprint, of a cell or particle, it is possible to not only detect its presence, but also determine what type of cell it is. The sensor can measure the membrane-induced shift in magnitude and phase of a cell's impedance at high frequencies. The AC impedance sensor of this invention can be used as a sample pre-treatment stage for autonomous chemical/biological warfare detection systems, or can be used as a sample preparation tool for other biological applications. Also, the impedance sensor can be used for sample pre-treatment for medical diagnostic systems, as well as for identification and sorting of cells such as for differential blood cell analysis.

While various embodiments, materials, parameters, etc., have been described and illustrated to exemplify and teach the principles of the invention, such are not intended to be limiting. Modifications and changes may become apparent to those skilled in the art, and it is intended that the invention be limited only by the scope of the appended claims.

What is claimed is:

1. A device including at least one microfabricated alternating current (AC) impedance sensor, including:
   at least one microfluidic channel for the passage therethrough of particle laden sample fluid,
   a first electrode located in the at least one microfluidic channel,
   a second electrode located adjacent the microfluidic channel and in spaced relation to said first electrode,
   an alternating current source operatively connected to said first and second electrodes, and
   means for electrically connecting said first and second electrodes to an impedance measuring circuit,
   whereby impedance between the first and second electrode is changed by particles or cells in the sample fluid passing through said microfluidc channel.

2. The impedance sensor of claim 1, wherein said microfluidic channel is located intermediate a pair of bonded members formed of material selected from the group consisting of glass, plastic, and non-conductive material.

3. The impedance sensor of claim 2, wherein one of said pair of bonded members includes a plurality of openings in alignment with said microfluidic channel and with said first and second electrodes, said openings functioning as a fluid inlet/outlet or as an electronic feedthrough for connecting said electrodes to said impedance measuring circuit.

4. The impedance sensor of claim 1, wherein said microfluidic channel is located within low parasitic capacitance material.

5. The impedance sensor of claim 1, wherein said first and second electrodes are composed of material selected from the group consisting of platinum and gold.

6. The impedance sensor of claim 5, wherein said first and second electrodes are composed of platinum with a chromium adhesion layer.

7. The impedance sensor of claim 6, wherein the platinum has a thickness of 0.1–0.2 microns and the chromium has a thickness of about 0.5 nm.

8. The impedance sensor of claim 1, wherein said first and second electrodes have a length of 10 $\mu$m to 200 $\mu$m and width of 10 $\mu$m to 200 $\mu$m.

9. The impedance sensor of claim 1, wherein said impedance measuring circuit comprises an integrated chip capable of measuring a plurality of frequencies simultaneously and eliminates a need for a reference channel.

10. The device of claim 9, comprising a microfluidic chip containing at least a sample input and a reference input in fluid communication with said at least two microfluidic channels, a fluid output in fluid communication with each of said microfluidic channels, three electrode contacts located adjacent said at least two microfluidic channels, and a fluid ground contact operatively connected to said sample input.

11. The device of claim 10, wherein at least said electrodes are composed of material selected from the group consisting of platinum and gold.

12. The AC sensor of claim 11, which has an operational bandwidth which approaches 10 MHz with a signal-to-noise ratio of about 40 dB.

13. The AC sensor of claim 11, includes an impedance measuring circuit constructed to measure particle impedance at three or more frequencies simultaneously, enabling derivation of multiple particle parameters.

14. The AC sensor of claim 11, including two identical microchannel sensors, one for sensing particles as they flow through a microchannel and other for use as an electrical reference.

15. The AC sensors of claim 11, wherein the two identical microchannel sensors are fabricated in a microfluidic chip mounted on a circuit board.

16. The AC sensors of claim 11, wherein the two identical microchannel sensors include a pair of microchannels, a sample input and a reference input connected to one end of each of said microchannels, a fluid output connected to opposite ends of said microchannels, three electrode contacts positioned adjacent said pair of microchannels, and a fluid ground contact electrically connected to said sample input.

17. The impedance sensor of claim 1, additionally including a reference electrode, said impedance measuring circuit being electrically connected to said reference electrode.

18. The device of claim 17, wherein adjacent of said three electrode contacts are electrically connected to electrodes located in one of the two microfluidic channels.

19. The device of claim 18, wherein at least said electrodes are constructed of platinum with a chromium adhesion layer.

20. The device of claim 1, having two identical AC impedance sensors and at least two microfluidic channels, one of said channels have a sample fluid therein, another of said channels having a reference fluid, said impedance measuring circuits containing electronics that simultaneously measure resistive and reactive changes in the differential impedance of the two sensors.

21. A microfluidc device operative connected to an impedance measuring circuit, comprising:

a pair of aligned and bonded glass members, at least one of said glass members having a microchannel therein, said at least one glass member having a pair of electrode pads located on a surface thereof and on opposite sides of said microchannel, an electrode located in said microchannel and electrically connected to one of said pair of electrode pads, another of said glass members having a plurality of openings extending therethrough, two of said openings being in alignment with said pair of electrode pads and at least one of said openings being in communication with said microchannel, said another of said glass members having an electrode located on a surface thereof adjacent said at least one of said glass members and electrically connected to another of said pair of electrode pads, and an alternating current source operatively connected to said electrodes, whereby said electrodes are electrically connected to said impedance measuring circuit via said two of said openings.

22. A microfabricated flow-through impedance characterization system capable of performing AC multi-frequency measurements on cells and other particles, comprising:

an AC sensor which measures both resistive and reactive impedance of passing particles at rates of up to 100 particles per second.

\* \* \* \* \*